United States Patent
Stafford et al.

[11] Patent Number: 5,600,305
[45] Date of Patent: Feb. 4, 1997

[54] PORTABLE PATIENT MONITORING SYSTEM

[76] Inventors: Jerome Stafford; Charles Bock, both of 3608 8th Ave. South, Great Falls, Mont. 59405

[21] Appl. No.: 533,259

[22] Filed: Sep. 25, 1995

[51] Int. Cl.⁶ .................................................. G08B 23/00
[52] U.S. Cl. ........................................ 340/573; 340/556
[58] Field of Search ................................... 340/556, 573, 340/555

[56] References Cited

U.S. PATENT DOCUMENTS

| | | | |
|---|---|---|---|
| 3,658,052 | 4/1972 | Alter | 340/573 |
| 4,196,425 | 4/1980 | Williams, Jr. et al. | 340/573 |
| 4,228,426 | 10/1980 | Roberts | 340/573 |
| 4,277,727 | 7/1981 | LeVert | 340/556 |
| 4,377,808 | 3/1983 | Kao | 340/527 |
| 4,893,005 | 1/1990 | Stiebel | 340/556 |
| 4,947,152 | 8/1990 | Hodges | 340/286.07 |
| 5,471,198 | 11/1995 | Newham | 340/556 |
| 5,486,810 | 1/1996 | Schwarz | 340/556 |

*Primary Examiner*—Jeffery Hofsass
*Assistant Examiner*—Mohammed R. Ghannam

[57] ABSTRACT

The present invention provides a simple, relatively inexpensive improved portable patient monitoring system that alerts a nurses station as well as the patient when the patient attempts to exit the hospital bed but that has no electronic components attached to the hospital bed. The portable patient monitoring system of the present invention comprises a portable master unit having an infrared emitter which emits an infrared beam and infrared detector which detects the infrared beam. The portable patient monitoring system of the present invention further comprises a portable external reflector which reflects the infrared beam emitted from the infrared emitter back to the infrared detector. The portable patient monitoring system further comprises comparing a signal from the infrared detector to a reference, outputting a signal from said comparison, sensing when the infrared beam has been broken and activating a local light on the portable master unit, a switch to a nurses station and a speech synthesis component to play a pre-recorded message.

The infrared emitter and infrared detector photo transistor are both contained in a single portable master unit which is placed adjacent to one end of the hospital bed. A portable external deflector is placed adjacent the other end of the hospital bed such that the infrared beam from the portable infrared emitter runs to the portable external deflector and back to the infrared detector photo transistor on a path parallel to the side of the hospital bed a predetermined distance away from the side of the hospital bed.

4 Claims, 2 Drawing Sheets

PORTABLE PATIENT MONITORING SYSTEM

BACKGROUND OF THE INVENTION

1. Field of the Invention

This invention pertains generally to improvements relating to systems for monitoring the activity of patients in hospital rooms, and specifically to a portable single sensor system for detecting the activity of a patient in a hospital bed.

2. Description of the Prior Art

Hospital patients are susceptible to serious injury in slip-and-fall accidents, particularly when attempting to exit their hospital beds. Hospital patients can be better protected from such injuries if hospital personnel could be adequately alerted in a timely manner to assist the patient and in turn hospital patients adequately warned in a timely manner to await assistance.

Hospital bed attachments are known which alert hospital personnel if a patient attempts to exit a hospital bed. U.S. Pat. No. 4,947,152, issued to Hodges on Aug. 7, 1990, discloses a patient monitoring apparatus comprising a detection means installed on a wall of a hospital room, which detection means generates an alert signal in response to presence of a patient in a predetermined zone spaced apart from the hospital bed, such predetermined zone generally includes a predetermined fanshaped zone extending from the detection means across the hospital room above and spaced apart from the hospital bed so the detection means does not respond to normal movement of the patient in the hospital bed.

U.S. Pat. No. 4,228,426, issued to Roberts on Oct. 4, 1980, discloses a patient monitoring apparatus comprising a switch installed in a pad positioned in the bedding of the hospital bed underneath a hospital patient. If the hospital patient gets up from the hospital bed, the switch contacts open, generating an alarm signal.

U.S. Pat. No. 4,196,425, issued to Williams, Jr., et al., on Apr. 1, 1980, discloses a photocell system wherein a plurality of optical energy emitters and photocells are installed in complementary locations on a hospital bed, generally at the head and foot of the hospital bed. If a hospital patient in such a hospital bed sits up or starts to get out of the hospital bed, an energy beam is interrupted and an alarm signal is produced.

Patient monitoring systems such as those disclosed by Roberts and Williams require that a sensing device be installed in the hospital bed and that a cable or other signal transmission means be used to connect said sensing device to an external circuit. Such a cable or other transmission means may pose a hazard to the hospital patient in the hospital bed as well as when the hospital patient is exiting the hospital bed. Such a cable or other transmission means may interfer with the making-up or moving of the hospital bed. Additionally, patient movement in the hospital bed may by itself contribute to a higher rate of false alarms. The patient monitoring system disclosed by Hodges provides a detection means remote from the hospital bed which is generally mounted relatively permanently on a hospital room wall and responds to movement in a predetermined fanshaped zone. Such a predetermined fanshaped zone may detect the presence of others in the hospital room such as when two hospital beds are located in the room and one of the hospital patients therein is receiving visitors or assistance. The predetermined fanshaped zone may not differentiate between single patients and others in the hospital room or movement by a hospital patient not receiving visitors or assistance, especially if the hospital beds are partitioned by means of a moveable partition or the like. Such lack of differentiation may decrease the efficiency and utility of such an apparatus.

Those skilled in the art are aware of the need for a simple, relatively inexpensive improved portable patient monitoring system remote from the hospital bed, which system monitors separate hospital beds and provides an alert to a nurses station as well as to the patient if the patient attempts to exit the hospital bed.

Therefore, it is an object of the present invention to provide a simple, relatively inexpensive improved portable patient monitoring system remote from the hospital bed, which system monitors separate hospital beds and provides an alert to a nurses station as well as to the patient if the patient attempts to exit the hospital bed.

SUMMARY OF THE INVENTION

The present invention accomplishes these objects by providing a simple, relatively inexpensive improved portable patient monitoring system that alerts a nurses station as well as the patient when the patient attempts to exit the hospital bed but that has no electronic components attached to the hospital bed. The portable patient monitoring system of the present invention comprises a portable master unit having an infrared emitter which emits an infrared beam and infrared detector which detects the infrared beam. The portable patient monitoring system of the present invention further comprises a portable external reflector which reflects the infrared beam emitted from the infrared emitter back to the infrared detector. The portable patient monitoring system further comprises comparing a signal from the infrared detector to a reference, outputting a signal from said comparison, sensing when the infrared beam has been broken and activating a local light on the portable master unit, a switch to a nurses station and a speech synthesis component to play a pre-recorded message.

The infrared emitter and infrared detector photo transistor are both contained in a single portable master unit which is placed adjacent to one end of the hospital bed. A portable external deflector is placed adjacent the other end of the hospital bed such that the infrared beam from the portable infrared emitter runs to the portable external deflector and back to the infrared detector photo transistor on a path parallel to the side of the hospital bed a predetermined distance away from the side of the hospital bed.

Electrical power is supplied to an external transformer from a standard wall outlet. The external transformer converts the wall outlet electrical power to low voltage (+12 volts DC), which low voltage then provides power for the portable patient monitoring system. The infrared detector is an infrared detector photo transistor which detects the reflected infrared beam and generates a signal therefrom. The infrared detector includes an alignment indicator. The alignment indicator monitors the alignment of the infrared beam between the infrared emitter, the external reflector and the infrared detector. Once activated and properly aligned, any movement which breaks the infrared beam between the infrared emitter, the external reflector and the infrared detector alerts hospital personnel.

IN THE DRAWINGS

DESCRIPTION OF THE PREFERRED EMBODIMENT

Figure 1:
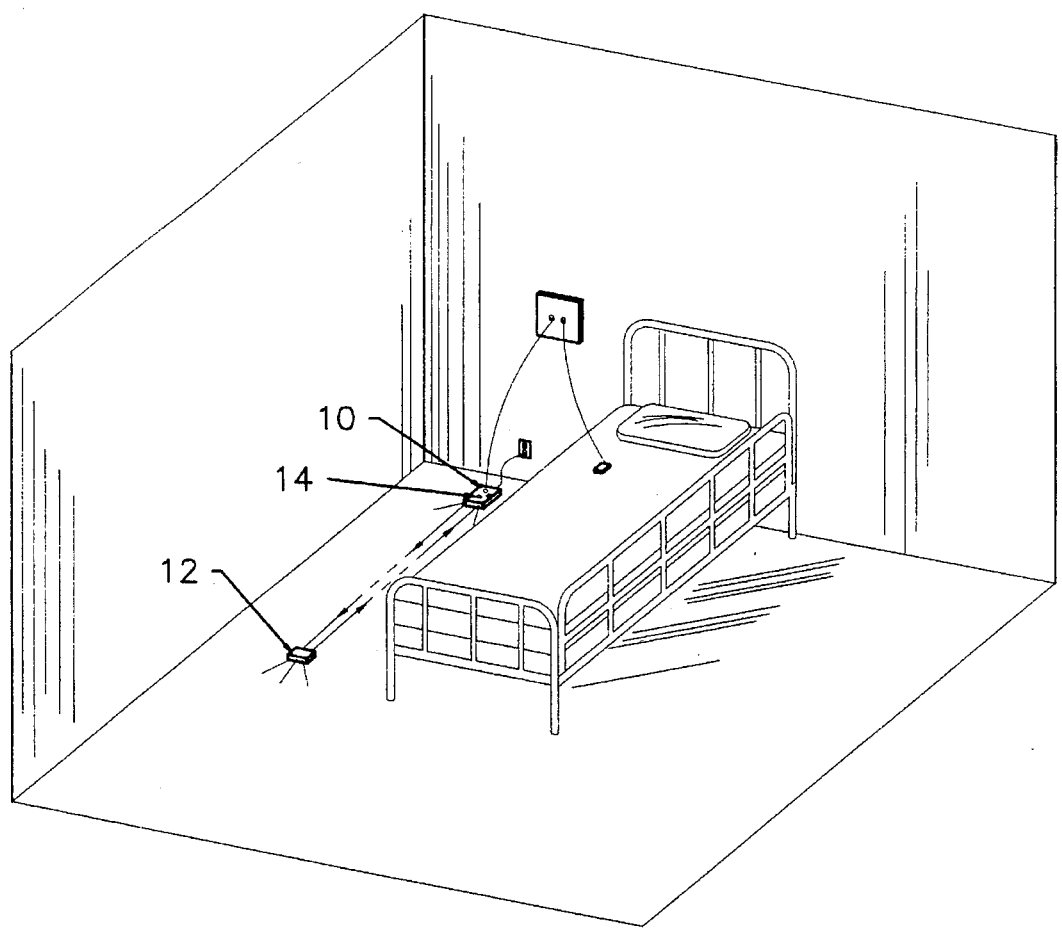
FIG. 1 is a perspective view of a portable patient monitoring system according to the present invention.

For a better understanding of the present invention, together with other and further objects, advantages and capabilities thereof, reference is made to the following disclosure and appended claims in connection with the above-described drawings. Referring now more particularly to the drawings, reference numerals will be used to denote like parts or structural features in the different views.

FIG. 1 shows a portable patient monitoring system of the present invention, which portable patient monitoring system is adapted to be used with a conventional nurses station call system or the like that may be provided in the rooms of a hospital, extended care facility or the like, said rooms having a hospital type bed for the individuals using such rooms. As used herein, a hospital type bed, or hospital bed, is a generally adjustable bed having passive restraints, such as railing, on one or both long sides of the bed.

In accordance with the present invention, a portable patient monitoring system is disclosed for use with a hospital bed and a generally conventional nurses station call system, which generally conventional nurses station call system has a communication panel located in a wall adjacent the hospital bed. The communication panel may include one or more recepticals for receiving a nurse call plug and be electrically connected to the nurses station or the like, which nurses station or the like may include lights and/or an audio communication system associated with separate hospital rooms or even separate hospital beds.

The portable patient monitoring system of the present invention comprises a portable master unit 10 having an infrared emitter which emits an infrared beam and infrared detector which detects the infrared beam. The portable patient monitoring system of the present invention further comprises a portable infrared reflector 12 which reflects the infrared beam emitted from the infrared emitter back to the infrared detector. The infrared detector compares a signal from the infrared reflector 12 to a reference and outputs a signal based upon said comparison. The infrared detector senses when the infrared beam has been broken and activates a local light 14 on the portable master unit 10, a switch to the central nursing station or the like and a speech synthesis component to play a pre-recorded message, which pre-recorded message repeats until a reset switch is pressed momentarily.

The portable patient monitoring system is adapted to use a transformer external to the portable master unit, which transformer receives electricity from a standard wall outlet. The transformer in turn provides electricity to the portable patient monitoring system. The transformer converts standard wall outlet electrical power to low voltage (+12 volts DC), which low voltage then provides power for the portable patient monitoring system.

Figure 2:
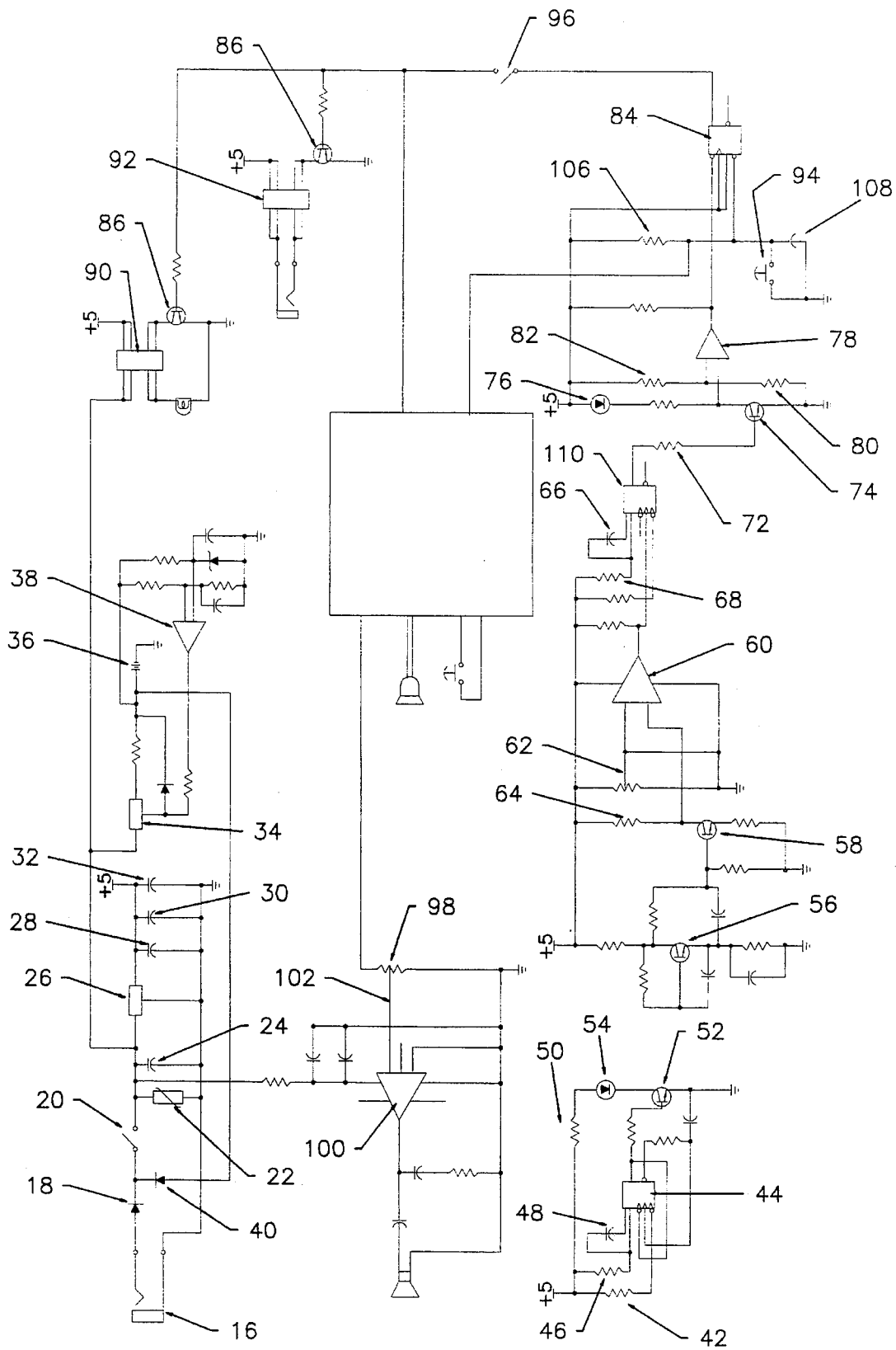
FIG. 2 is a circuit diagram of a portable patient monitoring system according to the present invention.

FIG. 2 shows +12 volts DC being supplied to the portable master unit from the transformer through a line 16. An inline diode 18 provides polarity protection to the portable master unit 10 from the incoming +12 volts DC. A switch 20 provides for on/off activation of the portable master unit 10. A metal oxide varistor 22 provides overvoltage protection to the portable master unit 10 from the incoming +12 volts DC. An input filter capacitor 24 is the input filter capacitor for a first three terminal regulator 26, which first three terminal regulator 26 is a fixed output (+5 volt DC) three terminal regulator. A plurality of three output capacitors 28, 30 and 32 are coupled in parallel with each other and coupled to said +5 volt fixed output and said first three terminal regulator 26, said plurality of three output capacitors 28, 30 and 32 and said first three terminal regulator 26 providing feeder +5 volts DC for the portable patient monitoring system.

A second three terminal regulator 34 is an adjustable three terminal regulator coupled to the +12 volt DC input, which second three terminal regulator 34 and +12 volt DC input provide a current source to charge a battery 36. The voltage to battery 36 is divided and compared to a reference voltage by a first voltage comparator 38. If the reference voltage is greater than the voltage to battery 36, the output of said first voltage comparator 38 will be high, enabling the output of said second three terminal regulator 34 to charge battery 36. When battery 36 has been charged sufficiently, the voltage to battery 36 will be higher than the reference voltage and the output of said first voltage comparator 38 will go low disabling the charging current. If the +12 volt DC input is not available to the portable master unit 10 from the transformer, battery 36 provides power to the portable master unit 10 through a diode 40.

The infrared emitter comprises a resistor 40, said resistor 40 being coupled to the feeder +5 volts DC and acting as a "pull-up" resistor to keep a dual retriggerable monostable multivibrator 44 set up as an astable multivibrator (an oscillator) in the enabled mode. The infrared emitter further comprises a resistor-capacitor network, said resistor-capacitor network having a second resistor 46 and a capacitor 48, said second resistor 46 and capacitor 48 providing a set time constant for said dual retriggerable monostable multivibrator 44. Said dual retriggerable monostable multivibrator 44 is coupled to a third resistor 50, said third resistor 50 in turn being coupled to the base of and driving a transistor 52, turning said transistor 52 on-off. Said transistor 52 in turn being coupled to and driving an infrared emitter 54, turning infrared emitter 54 on-off, said infrared emitter 54 emitting an infrared beam pulse which is reflected by said portable infrared reflector 12 and detected by the infrared detector.

The infrared detector comprises an infrared phototransistor 56, said infrared phototransistor 56 detecting and being driven by the infrared beam pulse received from said infrared emitter 54. Said infrared phototransistor 56 is coupled to a NPN transistor 58. Upon detecting said infrared beam, said infrared phototransistor 56 generates a pulse, said pulse being received by said NPN transistor 58. Said NPN transistor 58 further being coupled to a second voltage comparator 60. Upon receiving said pulse from said infrared phototransistor 56, said NPN transistor 58 generates a signal pulse, said signal pulse being received by said second voltage comparator 60. Said signal pulse being received by said second voltage comparator 60 from said NPN transistor 58 being dependent upon said infrared beam pulse being detected by said infrared phototransistor 56. Said second voltage comparator 60 is coupled to a wiper 62 of a variable resistor 64, said variable resistor 64 in turn being coupled between +5 volts DC from said feeder +5 volts DC and ground. Said second voltage comparator 60 compares the pulse level from said NPN transistor 58 and a static level generated by said variable resistor 64. Said second voltage comparator 60 is coupled to a second retriggerable monostable multivibrator 110. When the static level from said variable resistor 64 is adjusted to match said pulse level from said NPN transistor 58, the output of said second voltage comparator 60 will pulse, said pulse in turn driving said second retriggerable monostable multivibrator 110, said second retriggerable monostable multivibrator 110 being set up as a "one-shot". The time constant of the "one-shot" of said second retriggerable monostable multivibrator 110 being generated by a resistor-capacitor network having a resistor 66 and a capacitor 68. The time constant of the "one-shot" of said second retriggerable monostable multivibrator 110 being twice that of the time constant of said dual retriggerable monostable multivibrator 44. As long as pulses are being received by said second retriggerable monostable multivibrator 110, said second retriggerable monostable multivibrator 110 remains in a "triggered" mode. When said second retriggerable monostable multivibrator 110 is in the "triggered" mode, its output will remain high, which high output in turn activates a second NPN transistor 74. When the output of said second retriggerable monostable multivibrator 110 is high through a resistor 72, the high output will drive said second NPN transistor 74 to the "on" position. When said second NPN transistor 74 is at the "on" position, its collector will be low and an alignment indicator 76 will be "on" indicating that an unbroken infrared beam is being received by the infrared detector. Said NPN transistor 74 is coupled to the −input of a third voltage comparator 78. The +input of said third voltage comparator 78 is coupled to a voltage divider, said voltage divider comprising a plurality of two resistors 80 and 82, which plurality of two resistors 80 and 82 provide approximately 2.5 volts DC to the +input of said third voltage comparator 78.

When the infrared beam is broken, no pulses are driving said second retriggerable monostable multivibrator 110, and said second retriggerable monostable multivibrator 110 times out and goes to reset mode. When said second retriggerable monostable multivibrator 110 times out and goes to reset mode, its output goes low turning off said transistor 74. When said transistor 74 turns off, it turns off alignment indicator 76 and triggers said third voltage comparator 78. Triggering said third voltage comparator 78 drives its output low which presets a triggered data latch 84. Presetting said triggered data latch 84 causes its output to go high. When the output of said triggered data latch 84 goes high, it in turn drives a plurality of two transistors 86 and 88 which turn on a plurality of two relays 90 and 92, closes a dry contact out to a nurses station, turns on a local night light and enables an audio module 112 to play prerecorded message until an infrared beam is again present and a reset button 94 is pushed.

A switch 96 allows adjustment of the portable patient monitoring system without the prerecorded message playing, the local night light being on, or the contact being closed out to the nurses station.

The audio output from the audio module 112 is coupled to a variable resistor potentiometer 98, said variable resistor potentiometer 98 setting the audio output volume. A fourth voltage comparator 100 is coupled to the wiper 102 of said variable resistor potentiometer 98, said fourth voltage comparator 100 serving as an audio amplifier.

A switch 94 is coupled to said triggered data latch 84, said switch 94 resetting said triggered data latch 84 when pressed. Power is provided to said switch 94 by a resistor-capacitor network, said resistor-capacitor network having a resistor 106 and a capacitor 108.

In operation, the portable infrared emitter and infrared detector both contained in the portable master unit 10 are placed adjacent to one end of the hospital bed and the portable infrared reflector 12 is placed adjacent the other end of the hospital bed such that the infrared beam from the portable infrared emitter to the portable infrared reflector 12 and back to the infrared detector runs parallel to the side of the hospital bed a predetermined distance away from the side of the hospital bed. The portable patient monitoring system is thus adjacent to but remote from the hospital bed a predetermined distance such that the infrared beam runs parallel and adjacent to the side of the hospital bed which the patient could use for exiting the hospital bed. Typical hospital beds have railing restraints on both sides of the hospital bed to inhibit the patient exiting the hospital bed, and when portable patient monitoring system of the present invention is used with such a hospital bed, the railing restraint on the side of the hospital bed opposite the location of the portable patient monitoring system is positioned in place, thereby passively directing any attempt by the patient to exit the hospital bed toward the side of the hospital bed with the infrared beam of the portable patient monitoring system.

The infrared detector receives the infrared beam and generates a signal based on the existence thereof. The signal generated by the infrared detector is compared to an internal reference and when the signal generated by the infrared detector is not present, such as when the infrared beam is broken, a signal is activated to a local light 14 on the portable patient monitoring system, a signal is activated to the nurses station, and a signal is activated to the audio module 112 to play a pre-recorded message to the patient. The pre-recorded message plays until the reset switch is manually reset.

The audio module 112 operates in either play or record. A speaker is used to play the message and a microphone is used to record the message. The volume of the pre-recorded message is adjustable. Said switch 96 enables the hospital personnel to deactivate the portable patient monitoring system while attention is being provided to the patient. Once attention has been provided the patient, the hospital personnel can reactivate the portable patient monitoring system to resume monitoring of the patient by the portable patient monitoring system.

The portable patient monitoring system is adapted to communicate with a typical communication panel at the nurses station through a cable, with one end of the cable being plugged into the portable patient monitoring system and the other end being plugged into a standard receptical in the communication panel.

Once activated and properly aligned, any movement which alters or breaks the infrared beam between the infrared emitter, the infrared reflector 12 and the infrared detector activates the alarm system.

While a particular embodiment of the invention has been shown and described, it will be understood that the invention is not limited thereto, since modifications may be made that will become apparent to those skilled in the art.

What is claimed is:

1. A portable patient monitoring system adapted to be used with a conventional nurses station call system, a standard electrical wall outlet and a typical hospital type bed, said portable patient monitoring system comprising:

a portable master unit, said portable master unit being adapted to be placed adjacent to a typical hospital type bed;

said portable patient monitoring system having a transformer external to said portable master unit, said transformer being adapted to couple to a standard electrical wall outlet;

said transformer being adapted to convert standard electrical wall outlet electrical power to a low voltage (+12 volts DC), said low voltage (+12 volts DC) providing electrical power to said portable master unit;

said portable master unit having a line, said line providing said low voltage (+12 volts DC) to said portable master unit from said transformer;

said portable master unit having an inline diode, said inline diode being in said line and providing polarity protection to said portable master unit from said low voltage (+12 volts DC);

said portable master unit having a switch, said switch being in said line and providing on/off activation of said portable master unit;

said portable master unit having a metal oxide varistor, said metal oxide varistor being in said line and providing overvoltage protection to said portable master unit from said low voltage (+12 volts DC);

said portable master unit having an input filter capacitor, said input filter capacitor being in said line and being coupled to a first three terminal regulator, said three terminal regulator being a fixed output (+5 volts DC) three terminal regulator;

said portable master unit having a plurality of three output capacitors, said plurality of three output capacitors being coupled in parallel with each other as well as said low voltage (+12 volt DC) and said first three terminal regulator;

said plurality of three output capacitors and said first three terminal regulator providing a feeder +5 volts DC for said portable patient monitoring system;

said portable master unit having an a second three terminal regulator, said second three terminal regulator being adjustable and being coupled to said low voltage (+12 volt DC);

said second three terminal regulator being coupled and providing voltage to a battery;

said battery being coupled to a first voltage comparator, said first voltage comparator dividing and comparing said voltage to said battery to a reference voltage;

said battery being coupled to a diode;

said battery providing power to said portable master unit through said diode when said low voltage (+12 volt DC) is not available;

said portable master unit having an infrared emitter, said infrared emitter emitting an infrared beam;

said portable master unit having an infrared detector, said infrared detector detecting said infrared beam;

said portable patient monitoring system having a portable infrared reflector, said portable infrared reflector reflecting said infrared beam emitted from said infrared emitter back to said infrared detector; and, said portable infrared reflector being adapted to be placed adjacent to said typical hospital type bed such that said infrared beam from said portable infrared emitter to said portable infrared reflector and back to said infrared detector runs parallel to said typical hospital type bed a predetermined distance away from said typical hospital type bed.

2. A portable patient monitoring system according to claim 1 wherein said infrared emitter further comprises a resistor, said resistor being coupled to said feeder +5 DC volts and acting as a "pull-up" resistor;

said infrared emitter having a dual retriggerable monostable multivibrator, said dual retriggerable monostable multivibrator being coupled to said resistor and being set up as an astable multivibrator (an oscillator) in the enabled mode;

said infrared emitter having a resistor-capacitor network coupled to said dual retriggerable monostable multivibrator, said resistor-capacitor network having a second resistor and a capacitor;

said second resistor and said capacitor providing a set time constant for said dual retriggerable monostable multivibrator;

said dual retriggerable monostable multivibrator being coupled to a third resistor;

said third resistor being coupled to and driving a transistor, said transistor turning said transistor on-off;

said transistor being coupled to and driving an infrared emitter, said transistor turning said infrared emitter on-off; and, said infrared emitter emitting an infrared beam, said infrared beam being reflected by a portable infrared reflector and detected by an infrared detector.

3. A portable patient monitoring system according to claim 1 wherein said infrared detector further comprises an infrared phototransistor, said infrared phototransistor detecting and being driven by said infrared beam detected from said infrared emitter;

said infrared phototransistor generating a pulse upon detecting said infrared beam;

said infrared phototransistor being coupled to a NPN transistor, said NPN transistor receiving said pulse from said infrared phototransistor;

said NPN transistor generating a signal pulse upon said NPN transistor receiving said pulse from said infrared phototransistor;

said NPN transistor being coupled to a second voltage comparator, said signal pulse being generated by said NPN transistor being received by said second voltage comparator;

said signal pulse being received by said second voltage comparator from said NPN transistor being dependent upon said infrared beam pulse being detected by said infrared phototransistor;

said second voltage comparator being coupled to a wiper of a variable resistor, said variable resistor being coupled between +5 volts DC from said feeder +5 DC volts and ground;

said second voltage comparator comparing a level of said pulse from said NPN transistor and a static level generated by said variable resistor;

said second voltage comparator being coupled to a second retriggerable monostable multivibrator;

said static level from said variable resistor being adjusted to match said level of said pulse from said NPN transistor, said adjustment causing said second voltage comparator to pulse;

said pulse from said second voltage comparator driving said second retriggerable monostable multivibrator;

said second retriggerable monostable multivibrator being set up as a "one-shot", said "one-shot" having a time constant being generated by a resistor-capacitor network;

said resistor-capacitor network having a resistor and a capacitor;

said time constant of said "one-shot" of said second retriggerable monostable multivibrator being twice that of said time constant of said dual retriggerable monostable multivibrator;

said second retriggerable monostable multivibrator remaining in a "triggered" mode as long as said pulses are being received by said second retriggerable monostable multivibrator, said "triggered" mode causing an output of said second retriggerable monostable multivibrator to remain high;

said high output of said second retriggerable monostable multivibrator activating a second NPN transistor;

said activating of said second NPN transistor driving a resistor;

said driving of said resistor driving said second NPN transistor to an "on" position;

said second NPN transistor being at said "on" position causing an alignment indicator to be "on";

said alignment indicator being "on" indicating an unbroken infrared beam being received by said infrared detector;

said NPN transistor being coupled to an −input of a third voltage comparator;

said third voltage comparator having a +input coupled to a voltage divider, said voltage divider having a plurality of two resistors;

said plurality of two resistors and providing approximately 2.5 volts DC to said +input of said third voltage comparator;

said infrared beam being broken, no pulses are driving said second retriggerable monostable multivibrator, and said second retriggerable monostable multivibrator times out and goes to reset mode;

said second retriggerable monostable multivibrator timing out and going to reset mode, said output of said second retriggerable monostable multivibrator goes low turning off said transistor;

said transistor turning off said alignment indicator and triggers said third voltage comparator;

said third voltage comparator being triggered drives said output of said third voltage comparator low;

said output of said third voltage comparator being low presetting a triggered data latch;

said triggered data latch being preset causing an output of said triggered data latch to go high;

said output of said triggered data latch going high driving a plurality of two transistors;

said plurality of two transistors being driven turning on a plurality of two relays;

said plurality of two transistors being driven closing a contact out to a nurses station;

said plurality of two transistors being driven turning on a local night light;

said plurality of two transistors being driven enabling an audio module to play prerecorded message;

said plurality of two transistors being driven until said infrared beam is again present and until a reset button is pushed a switch coupled to said plurality of two transistors allowing adjustment of said portable patient monitoring system without said prerecorded message playing, said local night light being on, or said contact being closed out to the nurses station;

said audio module being coupled to a variable resistor potentiometer, said variable resistor potentiometer setting an audio output volume;

said variable resistor potentiometer having a wiper;

said wiper of said variable resistor potentiometer being coupled to a fourth voltage comparator, said fourth voltage comparator serving as an audio amplifier;

said triggered data latch being coupled to a switch, said switch resetting said triggered data latch;

said switch being coupled to a resistor-capacitor network, said resistor-capacitor network having a resistor and a capacitor; and, said resistor-capacitor network providing power to said switch for resetting said triggered data latch.

4. A portable patient monitoring system according to claim 2 wherein said infrared detector further comprises an infrared phototransistor, said infrared phototransistor detecting and being driven by said infrared beam detected from said infrared emitter;

said infrared phototransistor generating a pulse upon detecting said infrared beam;

said infrared phototransistor being coupled to a NPN transistor, said NPN transistor receiving said pulse from said infrared phototransistor;

said NPN transistor generating a signal pulse upon said NPN transistor receiving said pulse from said infrared phototransistor;

said NPN transistor being coupled to a second voltage comparator, said signal pulse being generated by said NPN transistor being received by said second voltage comparator;

said signal pulse being received by said second voltage comparator from said NPN transistor being dependent upon said infrared beam pulse being detected by said infrared phototransistor;

said second voltage comparator being coupled to a wiper of a variable resistor, said variable resistor being coupled between +5 volts DC from said feeder +5 DC volts and ground;

said second voltage comparator comparing a level of said pulse from said NPN transistor and a static level generated by said variable resistor;

said second voltage comparator being coupled to a second retriggerable monostable multivibrator;

said static level from said variable resistor being adjusted to match said level of said pulse from said NPN transistor, said adjustment causing said second voltage comparator to pulse;

said pulse from said second voltage comparator driving said second retriggerable monostable multivibrator;

said second retriggerable monostable multivibrator being set up as a "one-shot", said "one-shot" having a time constant being generated by a resistor-capacitor network;

said resistor-capacitor network having a resistor and a capacitor;

said time constant of said "one-shot" of said second retriggerable monostable multivibrator being twice that of said time constant of said dual retriggerable monostable multivibrator;

said second retriggerable monostable multivibrator remaining in a "triggered" mode as long as said pulses are being received by said second retriggerable monostable multivibrator, said "triggered" mode causing an output of said second retriggerable monostable multivibrator to remain high;

said high output of said second retriggerable monostable multivibrator activating a second NPN transistor to an "on" position;

said second NPN transistor being at said "on" position causing an alignment indicator to be "on";

said alignment indicator being "on" indicating an unbroken infrared beam being received by said infrared detector;

said NPN transistor being coupled to an −input of a third voltage comparator;

said third voltage comparator having a +input coupled to a voltage divider, said voltage divider having a plurality of two resistors;

said plurality of two resistors and providing approximately 2.5 volts DC to said +input of said third voltage comparator;

said infrared beam being broken, no pulses are driving said second retriggerable monostable multivibrator, and said second retriggerable monostable multivibrator times out and goes to reset mode;

said second retriggerable monostable multivibrator timing out and going to reset mode, said output of said second retriggerable monostable multivibrator goes low turning off said transistor;

said transistor turning off turns off said alignment indicator and triggers said third voltage comparator;

said third voltage comparator being triggered drives said output of said third voltage comparator low;

said output of said third voltage comparator being low presetting a triggered data latch;

said triggered data latch being preset causing an output of said triggered data latch to go high;

said output of said triggered data latch going high driving a plurality of two transistors;

said plurality of two transistors being driven turning on a plurality of two relays;

said plurality of two transistors being driven closing a contact out to a nurses station;

said plurality of two transistors being driven turning on a local night light;

said plurality of two transistors being driven enabling an audio module to play prerecorded message;

said plurality of two transistors being driven until said infrared beam is again present and until a reset button is pushed a switch coupled to said plurality of two transistors allowing adjustment of said portable patient monitoring system without said prerecorded message playing, said local night light being on, or said contact being closed out to the nurses station;

said audio module being coupled to a variable resistor potentiometer, said variable resistor potentiometer setting an audio output volume;

said variable resistor potentiometer having a wiper;

said wiper of said variable resistor potentiometer being coupled to a fourth voltage comparator, said fourth voltage comparator serving as an audio amplifier;

said triggered data latch being coupled to a switch, said switch resetting said triggered data latch;

said switch being coupled to a resistor-capacitor network, said resistor-capacitor network having a resistor and a capacitor; and, said resistor-capacitor network providing power to said switch for resetting said triggered data latch.

* * * * *